United States Patent
Akabas et al.

(10) Patent No.: US 10,648,012 B2
(45) Date of Patent: May 12, 2020

(54) ASSAY FOR INHIBITORS OF EQUILIBRATIVE OR CONCENTRATIVE NUCLEOSIDE TRANSPORTERS

(71) Applicant: ALBERT EINSTEIN COLLEGE OF MEDICINE OF YESHIVA UNIVERSITY, Bronx, NY (US)

(72) Inventors: Myles Akabas, Scarsdale, NY (US); Ithiel James Frame, Bronx, NY (US); Roman Deniskin, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 651 days.

(21) Appl. No.: 14/759,973

(22) PCT Filed: Jan. 8, 2014

(86) PCT No.: PCT/US2014/010626
§ 371 (c)(1),
(2) Date: Jul. 9, 2015

(87) PCT Pub. No.: WO2014/110097
PCT Pub. Date: Jul. 17, 2014

(65) Prior Publication Data
US 2016/0010134 A1    Jan. 14, 2016

Related U.S. Application Data

(60) Provisional application No. 61/751,024, filed on Jan. 10, 2013, provisional application No. 61/828,278, filed on May 29, 2013, provisional application No. 61/874,391, filed on Sep. 6, 2013.

(51) Int. Cl.
*C12Q 1/02* (2006.01)
*C07K 14/705* (2006.01)
*C12Q 1/18* (2006.01)
*C07K 14/44* (2006.01)
*C07K 14/445* (2006.01)

(52) U.S. Cl.
CPC .............. *C12Q 1/025* (2013.01); *C07K 14/44* (2013.01); *C07K 14/445* (2013.01); *C07K 14/705* (2013.01); *C12Q 1/18* (2013.01)

(58) Field of Classification Search
None
See application file for complete search history.

(56) References Cited

PUBLICATIONS

Zhang et al., Molecular Pharmacology, 2005, vol. 68 pp. 830-839.*
Hyde et al., Molecular Membrane Biology, 2001, vol. 18, pp. 53-63.*
Warnick et al., Cancer Research, 1972, vol. 32, pp. 2017-2022.*
Downie et al., The Journal of Biological Chemistry, 2010, vol. 285, pp. 20827-20833.*
PCT International Search Report and Written Opinion, dated Aug. 28, 2014 in connection with PCT International Application No. PCT/US2014/10626, 9 pages.
Vickers M F et al., entitled "Functional production and reconstitution of the human equilibrative nucleotide transporter (hENT1) in *Saccharomyces cerevisiae*," Biochem. J. (1999) 339, 21-32.
Hutchins G G et al., entitled "Gene Knockout/Gene Therapy in Yeast Using Homologous Recombination," Association for Biology Laboratory Education (ABLE) 2008 Proceedings, vol. 30:49-62.

* cited by examiner

*Primary Examiner* — Mindy G Brown
(74) *Attorney, Agent, or Firm* — Amster, Rothstein & Ebenstein LLP (57) ABSTRACT

Methods and systems for identifying inhibitors of Equilibrative Nucleoside Transporters are provided. Methods and systems for identifying inhibitors of Concentrative Nucleoside Transporters are also provided.

10 Claims, 6 Drawing Sheets

ASSAY FOR INHIBITORS OF EQUILIBRATIVE OR CONCENTRATIVE NUCLEOSIDE TRANSPORTERS

CROSS-REFERENCE TO RELATED APPLICATIONS

This application is a U.S. national stage entry under 35 U.S.C. § 371 of PCT International Patent Application No. PCT/US2014/010626, filed on Jan. 8, 2014, which claims the benefit of U.S. Provisional Application No. 61/751,024, filed Jan. 10, 2013, and of U.S. Provisional Application No. 61/828,278, filed May 29, 2013, and of U.S. Provisional Application No. 61/874,391, filed Sep. 6, 2013, the contents of each of which are hereby incorporated by reference.

STATEMENT OF GOVERNMENT SUPPORT

This invention was made with government support under grant number T32-GM007288 awarded by the National Institutes of Health. The government has certain rights in this invention.

BACKGROUND OF THE INVENTION

Throughout this application various publications are referred to by number in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Some eukaryotic parasites, such as *Plasmodium* species that cause malaria, *Leshmania* species that cause leshmaniasis, *Trypanasoma* species that cause African sleeping sickness, Chagas disease and *Toxoplasma gondii* that causes toxoplasmosis, and *Cryptosporidium* which causes cryptosporidiosis, are purine auxotrophs, unable to perform de novo purine biosynthesis [3-7]. Because nucleobases and nucleosides are impermeable through phospholipid cell membranes, cells use Equilibrative Nucleoside Transporters (ENTs) and Concentrative Nucleoside Transporters (CNTs) to import and export purines and pyrimidines [1,2]. The parasites rely on purine import via ENTs, and possibly CNTs, to supply purines needed for DNA synthesis and other cellular processes. The imported purines are processed through the purine salvage pathway to generate the specific purines required by the cell.

Blocking purine import is likely to have inhibitory or cytotoxic effects on these parasites. For example, knockout of the *Plasmodium falciparum* Equilibrative Nucleoside Transporter Type 1 (PfENT1) results in parasites that are not viable during in vitro culture in growth media containing physiological purine concentrations found in normal human blood [8,9].

ENTs are also present in humans where they are responsible for clearance of nucleobases and nucleosides from the plasma and extracellular space to terminate purinergic signaling [10-13]. Human ENTs are about 18% sequence identical with PfENT1. It is reasonable to expect that species specific ENT inhibitors exist. Supporting this, human ENT inhibitors, dipyridamole, dilazep and p-nitrobenzylthioinosine, do not inhibit PfENT1. In addition, dipyridamole and dilazep are in clinical use as coronary artery vasodilators and antiplatelet agents. Thus, ENT inhibitors are useful therapeutic agents for modulating purinergic signaling pathways. Moreover, some cancer cells are unable to perform de novo purine biosynthesis and are reliant on purine uptake for DNA replication. ENT inhibitors can serve as anti-cancer drugs for this limited group of cancers.

The present invention discloses a novel high throughput assay and system for identifying ENT inhibitors.

SUMMARY OF THE INVENTION

A recombinant yeast comprising a deletion of gene in the yeast de novo purine biosynthetic pathway in the genome thereof and expressing a heterologous equilibrative nucleoside transporter (ENT) or a heterologous concentrative nucleoside transporter (CNT).

A recombinant yeast comprising a deletion of an fui1 gene and/or ade2 gene in the genome thereof and expressing a heterologous equilibrative nucleoside transporter (ENT).

A recombinant yeast comprising a deletion of an fui1 gene and/or ade2 gene in the genome thereof and expressing a heterologous concentrative nucleoside transporter (CNT).

A recombinant yeast comprising a deletion of a *Saccharomyces cerevisiae* gene ADE4; ADE5; ADE7; ADE8; ADE6; ADE1; ADE2; ADE13; ADE16; ADE17; or ADE12; or an equivalent gene of one thereof in another yeast strain, and expressing a heterologous equilibrative nucleoside transporter (ENT) or a heterologous concentrative nucleoside transporter (CNT).

A system is provided comprising the recombinant yeast in a yeast culture medium comprising a cytotoxic nucleoside.

A method is provided for identifying an agent as an inhibitor of an equilibrative nucleoside transporter (ENT) comprising
contacting a recombinant yeast as described herein in the presence of a cytotoxic nucleoside and in a yeast culture medium with the agent for a first predetermined time period under conditions permitting yeast growth,
quantifying the growth of the recombinant yeast in the presence of the agent,
comparing the growth of the recombinant yeast in the presence of the agent to the growth of the recombinant yeast for a second predetermined time period in the absence of the agent,
and identifying the agent as an inhibitor or not of the ENT, wherein an increased growth in the presence of the agent as compared to in the absence of the agent indicates that the agent is an inhibitor of the ENT, and wherein no increase in, or a decrease in growth, in the presence of the agent as compared to in the absence of the agent indicates that the agent is not an inhibitor of the ENT.

A method is provided for identifying an agent as an inhibitor of a concentrative nucleoside transporter (CNT) comprising
contacting a recombinant yeast as described herein in the presence of a cytotoxic nucleoside and in a yeast culture medium with the agent for a first predetermined time period under conditions permitting yeast growth,
quantifying the growth of the recombinant yeast in the presence of the agent, comparing the growth of the recombinant yeast in the presence of the agent to the growth of the recombinant yeast for a second predetermined time period in the absence of the agent,
and identifying the agent as an inhibitor or not of the CNT, wherein an increased growth in the presence of the agent as compared to in the absence of the agent indicates that the agent is an inhibitor of the CNT, and wherein no increase in, or a decrease in growth, in the presence of the agent as compared to in the absence of the agent indicates that the agent is not an inhibitor of the CNT A method for identifying an agent as an inhibitor of an equilibrative nucleoside transporter (ENT) or of a concentrative nucleoside transporter (CNT) comprising
contacting the recombinant yeast of as described herein having a deletion in a gene involved in the yeast de novo purine biosynthetic pathway in the presence of a nucleoside and in the substantial absence of purines, and in a yeast culture medium with the agent for a first predetermined time period under conditions permitting yeast growth,
quantifying the growth of the recombinant yeast in the presence of the agent,
comparing the growth of the recombinant yeast in the presence of the agent to the growth of the
recombinant yeast for a second predetermined time period in the absence of the agent and in the presence of a nucleoside and in the substantial absence of purines,
and identifying the agent as an inhibitor or not of the ENT, or CNT, respectively,
wherein an decreased growth in the presence of the agent as compared to in the absence of the agent indicates that the agent is an inhibitor of the ENT, or CNT, respectively,
and wherein no increase in, or a increase in growth, in the presence of the agent as compared to in the absence of the agent indicates that the agent is not an inhibitor of the ENT, or CNT, respectively.

A method for identifying an agent as an inhibitor of an equilibrative nucleoside transporter (ENT) comprising
contacting the recombinant yeast of as described herein having a deletion in an ade2 gene in the presence of a nucleoside and in the substantial absence of purines, and in a yeast culture medium with the agent for a first predetermined time period under conditions permitting yeast growth,
quantifying the growth of the recombinant yeast in the presence of the agent,
comparing the growth of the recombinant yeast in the presence of the agent to the growth of the recombinant yeast for a second predetermined time period in the absence of the agent and in the presence of a nucleoside and in the substantial absence of purines,
and identifying the agent as an inhibitor or not of the ENT, wherein an decreased growth in the presence of the agent as compared to in the absence of the agent indicates that the agent is an inhibitor of the ENT, and wherein no increase in, or a increase in growth, in the presence of the agent as compared to in the absence of the agent indicates that the agent is not an inhibitor of the ENT.

DETAILED DESCRIPTION OF THE INVENTION

A recombinant yeast comprising a deletion of gene in the yeast de novo purine biosynthetic pathway in the genome thereof and expressing a heterologous equilibrative nucleoside transporter (ENT) or a heterologous concentrative nucleoside transporter (CNT).

A recombinant yeast comprising a deletion of an fui1 gene and/or ade2 gene in the genome thereof and expressing a heterologous equilibrative nucleoside transporter (ENT).

A recombinant yeast comprising a deletion of an fui1 gene and/or ade2 gene in the genome thereof and expressing a heterologous concentrative nucleoside transporter (CNT).

In an embodiment, the deletion is such that the recombinant yeast is unable to express any product from the fui1 gene. The ENT is encoded by a heterologous nucleic acid transformed into the recombinant yeast. The heterologous nucleic acid may be in the form of a plasmid and can comprise, for example, one or more of a promoter sequence and an antibiotic resistance gene. Stable and temporary transformation of yeast with heterologous nucleic acids are known in the art, and encompassed within the invention. The ENT is heterologous with respect to the yeast, in that it is not naturally present in that yeast species.

In an embodiment, the CNT is encoded by a heterologous nucleic acid transformed into the recombinant yeast. The heterologous nucleic acid may be in the form of a plasmid and can comprise, for example, one or more of a promoter sequence and an antibiotic resistance gene. Stable and temporary transformation of yeast with heterologous nucleic acids are known in the art, and encompassed within the invention. The CNT is heterologous with respect to the yeast, in that it is not naturally present in that yeast species.

In a preferred embodiment of the recombinant yeasts, methods and systems described herein, the yeast is a strain having de novo purine synthesis capability. In an embodiment, the yeast is a strain having no other ENT encoding gene other than an Fui1 gene or homolog. In an embodiment, the yeast is a strain having no other ENT encoding or CNT encoding gene other than an Fui1 gene or homolog. In a preferred embodiment, the yeast is *Saccharomyces cervisiae*.

In a preferred embodiment of the recombinant yeasts, methods and systems described herein, the heterologous ENT is a parasite ENT. In a preferred embodiment of the recombinant yeasts, methods and systems described herein, the heterologous CNT is a parasite CNT.

In an embodiment, the parasite is a purine auxotroph. In an embodiment, the parasite is a *Plasmodium* sp., *Leishmania* sp., *Trypanasoma* sp., *Toxoplasma* sp., *Entamoeba* sp., *Schistosoma* sp., or *Cryptosporidium* sp.

In an embodiment, the ENT is a *Plasmodium falciparum* ENT type 1. In an embodiment, the ENT is an ENT4 (see 19).

In an embodiment of the recombinant yeasts, methods and systems described herein, the heterologous ENT is a mammalian ENT. In an embodiment, the heterologous ENT is a human ENT.

In an embodiment of the recombinant yeasts, methods and systems described herein, the ENT is an ENT1, an ENT2, an ENT3, or an ENT4. In an embodiment, the ENT is an ENT1 encoded by the SLC29A1 Gene. For example, see RefSeq NP_001071642.1. In an embodiment, the ENT is an ENT2 encoded by the SLC29A2 Gene. For example, see RefSeq NP_001523.2. In an embodiment, the ENT is a *Cryptosporidium* ENT. In an embodiment, the ENT is encoded by an ENT gene having the same sequence as an ENT gene of a *C. parvum* or of a *C. hominis*.

In an embodiment of the recombinant yeasts, methods and systems described herein, the gene in the yeast de novo purine biosynthetic pathway comprises a *Saccharomyces cerevisiae* gene ADE4; ADE5; ADE7; ADE8; ADE6; ADE1; ADE2; ADE13; ADE16; ADE17; or ADE12; or an equivalent gene of one thereof in another yeast strain.

A system is provided comprising a recombinant yeast as described herein in a yeast culture medium comprising a cytotoxic nucleoside.

In an embodiment of the systems and methods described herein, the cytotoxic nucleoside is 5-fluorouridine, 7-deazaadenosine or tubercidin. In a preferred embodiment, the cytotoxic nucleoside is 5-fluorouridine.

In an embodiment of the systems and methods described herein, the system comprises a high throughput assay plate comprising a plurality of individual wells and wherein the yeast culture medium is contained within one or more wells of the plurality.

In an embodiment of the systems and methods described herein, the cytotoxic nucleoside is present in the yeast growth medium at a level which has been predetermined to be the minimum concentration of cytotoxic nucleoside that causes complete killing of the recombinant yeast. This is readily determined by one of ordinary skill in the art.

In an embodiment, each well comprises a plurality of the recombinant yeasts, with each well only containing recombinant yeasts comprising a single type of heterologous nucleic acid.

A method for identifying an agent as an inhibitor of an equilibrative nucleoside transporter (ENT) comprising contacting the recombinant yeast of as described herein having a deletion in an ade2 gene in the presence of a nucleoside and in the substantial absence of purines, and in a yeast culture medium with the agent for a first predetermined time period under conditions permitting yeast growth,
quantifying the growth of the recombinant yeast in the presence of the agent,
comparing the growth of the recombinant yeast in the presence of the agent to the growth of the recombinant yeast for a second predetermined time period in the absence of the agent and in the presence of a nucleoside and in the substantial absence of purines,
and identifying the agent as an inhibitor or not of the ENT, wherein a decreased growth in the presence of the agent as compared to in the absence of the agent indicates that the agent is an inhibitor of the ENT, and wherein no increase in, or a increase in growth, in the presence of the agent as compared to in the absence of the agent indicates that the agent is not an inhibitor of the ENT.

A method is provided for identifying an agent as an inhibitor of an equilibrative nucleoside transporter (ENT) comprising
contacting a recombinant yeast as described herein in the presence of a cytotoxic nucleoside and in a yeast culture medium with the agent for a first predetermined time period under conditions permitting yeast growth,
quantifying the growth of the recombinant yeast in the presence of the agent,
comparing the growth of the recombinant yeast in the presence of the agent to the growth of the recombinant yeast for a second predetermined time period in the absence of the agent,
and identifying the agent as an inhibitor or not of the ENT, wherein an increased growth in the presence of the agent as compared to in the absence of the agent indicates that the agent is an inhibitor of the ENT, and wherein no increase in, or a decrease in growth, in the presence of the agent as compared to in the absence of the agent indicates that the agent is not an inhibitor of the ENT.

A method is provided for identifying an agent as an inhibitor of a concentrative nucleoside transporter (CNT) comprising
contacting a recombinant yeast as described herein in the presence of a cytotoxic nucleoside and in a yeast culture medium with the agent for a first predetermined time period under conditions permitting yeast growth,
quantifying the growth of the recombinant yeast in the presence of the agent,
comparing the growth of the recombinant yeast in the presence of the agent to the growth of the recombinant yeast for a second predetermined time period in the absence of the agent,
and identifying the agent as an inhibitor or not of the CNT, wherein an increased growth in the presence of the agent as compared to in the absence of the agent indicates that the agent is an inhibitor of the CNT, and wherein no increase in, or a decrease in growth, in the presence of the agent as compared to in the absence of the agent indicates that the agent is not an inhibitor of the CNT A method for identifying an agent as an inhibitor of an equilibrative nucleoside transporter (ENT) or of a concentrative nucleoside transporter (CNT) comprising contacting the recombinant yeast of as described herein having a deletion in a gene involved in the yeast de novo purine biosynthetic pathway in the presence of a nucleoside and in the substantial absence of purines, and in a yeast culture medium with the agent for a first predetermined time period under conditions permitting yeast growth,
quantifying the growth of the recombinant yeast in the presence of the agent,
comparing the growth of the recombinant yeast in the presence of the agent to the growth of the recombinant yeast for a second predetermined time period in the absence of the agent and in the presence of a nucleoside and in the substantial absence of purines,
and identifying the agent as an inhibitor or not of the ENT, or CNT, respectively,
wherein a decreased growth in the presence of the agent as compared to in the absence of the agent indicates that the agent is an inhibitor of the ENT, or CNT, respectively,
and wherein no increase in, or a increase in growth, in the presence of the agent as compared to in the absence of the agent indicates that the agent is not an inhibitor of the ENT, or CNT, respectively.

In a preferred embodiment of the methods, the yeast is *Saccharomyces cervisiae*. In an embodiment, the cytotoxic nucleoside is present at a level in the yeast growth medium which has been predetermined to be the minimum concentration that causes complete killing of the recombinant yeast. Examples of cytotoxic nucleosides are described herein. Yeast culture media permitting yeast growth are well known in the art.

In an embodiment, the growth of the recombinant yeast is measured indirectly by quantifying the optical density (OD) of the medium containing the recombinant yeast. In an embodiment, the OD is determined at 590-610 nm. In a preferred embodiment, the OD is determined at 600 nm.

The first predetermined time period is one sufficient to permit observable yeast growth under normal conditions. For example, a 12-16 hour period at 30° C. For example, a 12-30 hour period at 30° C. Any suitable time period may be chosen. The second predetermined time period, in an embodiment, is a control time period. In an embodiment, the second predetermined time period is the same length as the first predetermined time period. In an embodiment, the second predetermined time period is a different length than the first predetermined time period. The control time period can be normalized if necessary. Growth can be quantified by any technique known in the art, such as by rate (and extrapolated if desired), absolute level, by mass, by an indirect effect such as optical density.

In an embodiment, the agent is a small organic molecule of 2000 daltons or less. In an embodiment, the agent comprises an RNAi agent, and is an oligonucleotide. In an embodiment, the oligonucleotide is 35 nucleotides or less. In an embodiment, the RNAi agent comprises an siRNA or an shRNA. In an embodiment, the agent comprises an antibody or a fragment of an antibody.

In an embodiment, the method further comprises determining if an agent identified by the method as an inhibitor of the ENT inhibits growth of, or kills, a parasite in which the ENT is found in the wild type thereof, comprising contacting the parasite with the inhibitor and determining the growth or viability of the parasite in the presence of the agent.

In an embodiment, the method further comprises determining if an agent identified by the method as an inhibitor of the ENT is toxic to a mammalian cell comprising contacting the mammalian cell in culture with the agent and determining the viability of the mammalian cell in the presence of the agent.

In an embodiment, the method further comprises determining if an agent identified by the method as an inhibitor of the ENT is toxic to a cancer cell reliant on purine uptake for DNA replication, comprising contacting the cancer cell with the agent and determining the viability of the cancer cell in the presence of the agent.

In an embodiment, the method further comprises determining if an agent identified by the method as an inhibitor of the CNT inhibits growth of, or kills, a parasite in which the CNT is found in the wild type thereof, comprising contacting the parasite with the inhibitor and determining the growth or viability of the parasite in the presence of the agent.

In an embodiment, the method further comprises determining if an agent identified by the method as an inhibitor of the CNT is toxic to a mammalian cell comprising contacting the mammalian cell in culture with the agent and determining the viability of the mammalian cell in the presence of the agent.

In an embodiment, the method further comprises determining if an agent identified by the method as an inhibitor of the CNT is toxic to a cancer cell reliant on purine uptake for DNA replication, comprising contacting the cancer cell with the agent and determining the viability of the cancer cell in the presence of the agent.

In an embodiment, the purines discussed herein are one or more of adenosine, hypoxanthine or adenine. In an embodiment, "determining" as used herein means experimentally determining.

In an embodiment of the methods, the ENT is a *Plasmodium* sp., *Leishmania* sp., *Trypanasoma* sp., *Toxoplasma* sp., *Entamoeba* sp., *Schistosoma* sp., or *Cryptosporidium* sp. ENT. In an embodiment of the methods, the CNT is a *Plasmodium* sp., *Leishmania* sp., *Trypanasoma* sp., *Toxoplasma* sp., *Entamoeba* sp., *Schistosoma* sp., or *Cryptosporidium* sp. CNT.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Herein is disclosed are novel assays that can be used to perform a high throughput screen to identify ENT inhibitors or used to perform a high throughput screen to identify CNT inhibitors. To applicants' knowledge, no similar assay has been described to identify inhibitors of ENTs, CNTs or other transporters. Compounds identified in the screen as ENT inhibitors or CNT inhibitors can serve as, inter alia, novel antiparasitic drugs.

Example 1

Figure 1:
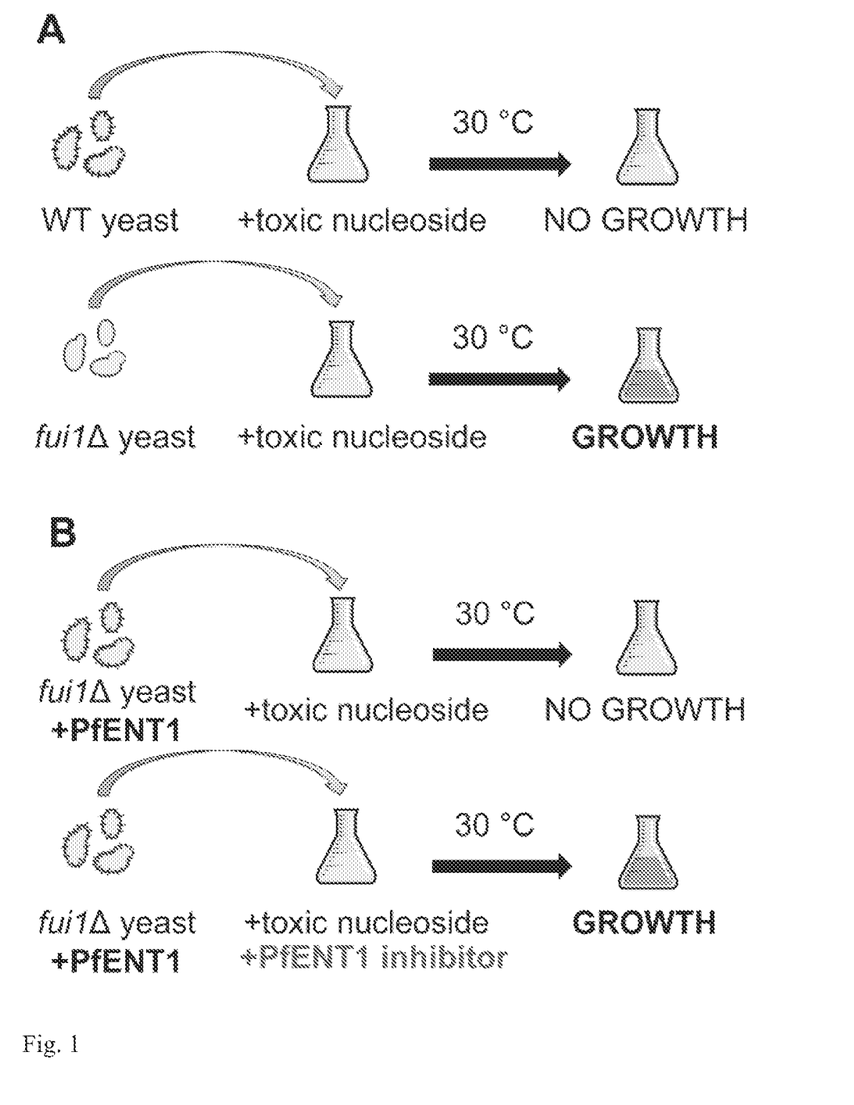
FIG. 1. Rationale for assay. (A) Untransfected WT and fui1Δ yeast. (B) PfENT1-expressing fui1Δ yeast.

The basis for the assay is that certain yeast, such as *Saccharomyces cerevisiae*, are capable of de novo purine biosynthesis. Thus, unlike *P. falciparum* or other purine auxotrophs, purine transporters are not essential for *S. cerevisiae* survival. The *S. cerevisiae* genome contains one gene, the fui1 gene (YBL042c), that codes for a plasma membrane purine/uridine transporter. fui1Δ gene knockout yeast are viable and are resistant to killing by the cytotoxic nucleoside analog 5-fluorouridine (5-FUrd) [14,15]. The ENT that is the proposed target for the assay must transport 5-FUrd or another cytotoxic nucleoside, such as tubercidin, that solely enters the yeast via the FUI1 transport pathway. To generate the yeast for the assay, the fui1Δ yeast are transformed with the gene encoding the target ENT in an appropriate expression plasmid. The ENT-expressing fui1Δ yeast are then tested for sensitivity to 5-FUrd or the appropriate cytotoxic nucleoside. With appropriate levels of ENT expression, the transformed fui1Δ yeast will be significantly more sensitive to killing than the parental fui1Δ yeast. Yeast growth can be monitored by the optical density at 600 nm ($OD_{600}$). Growth curves are determined for the ENT-expressing fui1Δ yeast to determine the length of time that it takes ~1–3×10$^6$ cells/ml to grow to an $OD_{600}$~1. The lowest concentration of the cytotoxic nucleoside that causes complete killing of the ENT-expressing fui1Δ yeast is identified in growth inhibition assays. The high throughput assay is then ready to screen for ENT inhibitors. ENT inhibitors will prevent uptake of the cytotoxic nucleoside and permit the yeast to grow (FIG. 1).

In an embodiment, the assay can be run as follows:
Wells in a high throughput assay plate are inoculated with ENT-expressing fui1Δ yeast ~1–3×10⁶ cells/ml ($OD_{600}$~0.1) in yeast growth media.
Aliquots of test drugs are added to each well at appropriate concentrations.
Cytotoxic nucleoside is added at the lowest concentration identified to cause complete killing.
Plates are incubated at 30° C. for an appropriate time (e.g. ~12-16 hrs) for the ENT-expressing fui1Δ yeast to grow to an $OD_{600}$~1.
For each well the $OD_{600}$ is measured. In wells with significant yeast growth the compounds added are identified as ENT inhibitors.

Secondary assays are used to demonstrate efficacy and specificity of the compound's effects: to demonstrate desired effects (e.g. cytotoxic effects against parasites for inhibitors of parasite ENTs; vasodilation, antiplatelet effects or other physiological effects for compounds directed against human ENTs); target specificity, if compounds are directed against a parasite ENT this will need to be assesses for effects on human ENTs; and to determine whether the compounds identified have cytotoxic effects against mammalian cells in culture.

Assay with PfENT1: PfENT1 transports 5-fluorouridine (5-FUrd). Previous work showed that PfENT1-expressing *Xenopus laevis* (frog) oocytes transport uracil and uridine [16]. It is demonstrated that increasing concentrations of 5-FUrd inhibit the uptake of [³H]-adenine by PfENT1-expressing oocytes with a $K_i$=1.1 mM. This is consistent with the transport of 5-FUrd by PfENT1.

Generation of PfENT1-expressing fui1Δ yeast. A yeast codon-optimized PfENT1 construct was generated with an HA epitope tag at its C-terminus. This construct was cloned into the pYMN11 plasmid under the regulation of the CYC1 promoter [17]. PCR amplified plasmid DNA containing 40-90 bp regions identical to those flanking the fui1 gene was transformed into fui1Δ yeast and selected on norseothricin antibiotic containing agar plates.

Figure 2:
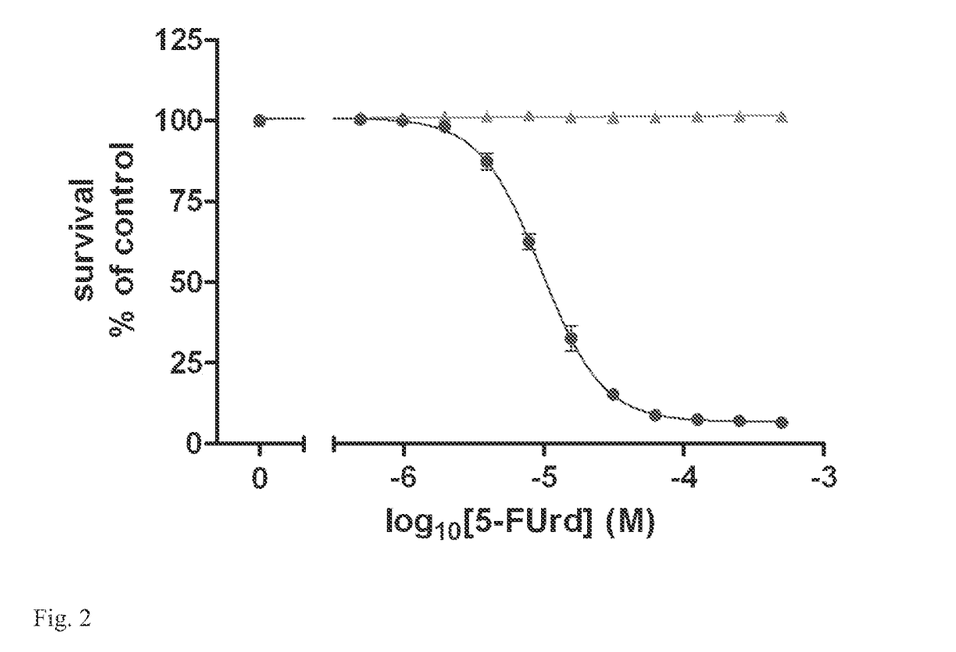
FIG. 2. 5-FUrd cytotoxicity assay. Concentration-response curves for 5 FUrd killing of PfENT1-expressing fui1Δ (circles) and fui1Δ (triangles) yeast. PfENT1-expressing fui1Δ IC$_{50}$=12 µM; fui1Δ IC$_{50}$=6400 µM FIG. 3. Plate uniformity and signal variability assay for PfENT1-expressing fui1Δ yeast grown with no 5-FUrd (max), 12 µM (mid) or 63 µM 5-FUrd (min), assay conditions described in text.

Concentration dependence of 5-FUrd cytotoxic effects on PfENT1-expressing fui1Δ *S. cerevisiae* and on the parental fui1Δ strain: To determine the dose-response relationship for killing by 5 FUrd, 200 μl cultures in rich media (yeast extract, peptone, 2% dextrose, YPD) were inoculated with 3×10⁶ cells/ml of PfENT1-expressing fui1Δ yeast and fui1Δ yeast. The cultures were grown in 96-well microtiter plates at 30° C., without shaking, in the absence of and in the presence of increasing concentrations of 5-FUrd (range 0.1-1,000 μM). After 570 minutes, the $OD_{600}$ was measured using a BioRad Benchmark Plus microplate reader to determine the extent of cell growth. The $OD_{600}$ was plotted as a function of drug concentration and the $IC_{50}$ for 5-FUrd was calculated (FIG. 2). These results demonstrate that 5-FUrd kills PfENT1-expressing fui1Δ yeast with an $IC_{50}$=12 μM. As expected, in the parental fui1Δ yeast, the 5-FUrd $IC_{50}$ is much higher, 6,400±1,800 μM (n=3) (FIG. 2). Though yeast grow optimally with constant aeration, a similar 5-FUrd $IC_{50}$ was obtained for PfENT1-expressing fui1Δ yeast whether the plate was shaken continuously at 200 rpm or unshaken for 570 minutes of growth ($IC_{50}$=9 μM). This demonstrated that shaking the cultures was unnecessary.

Figure 3:
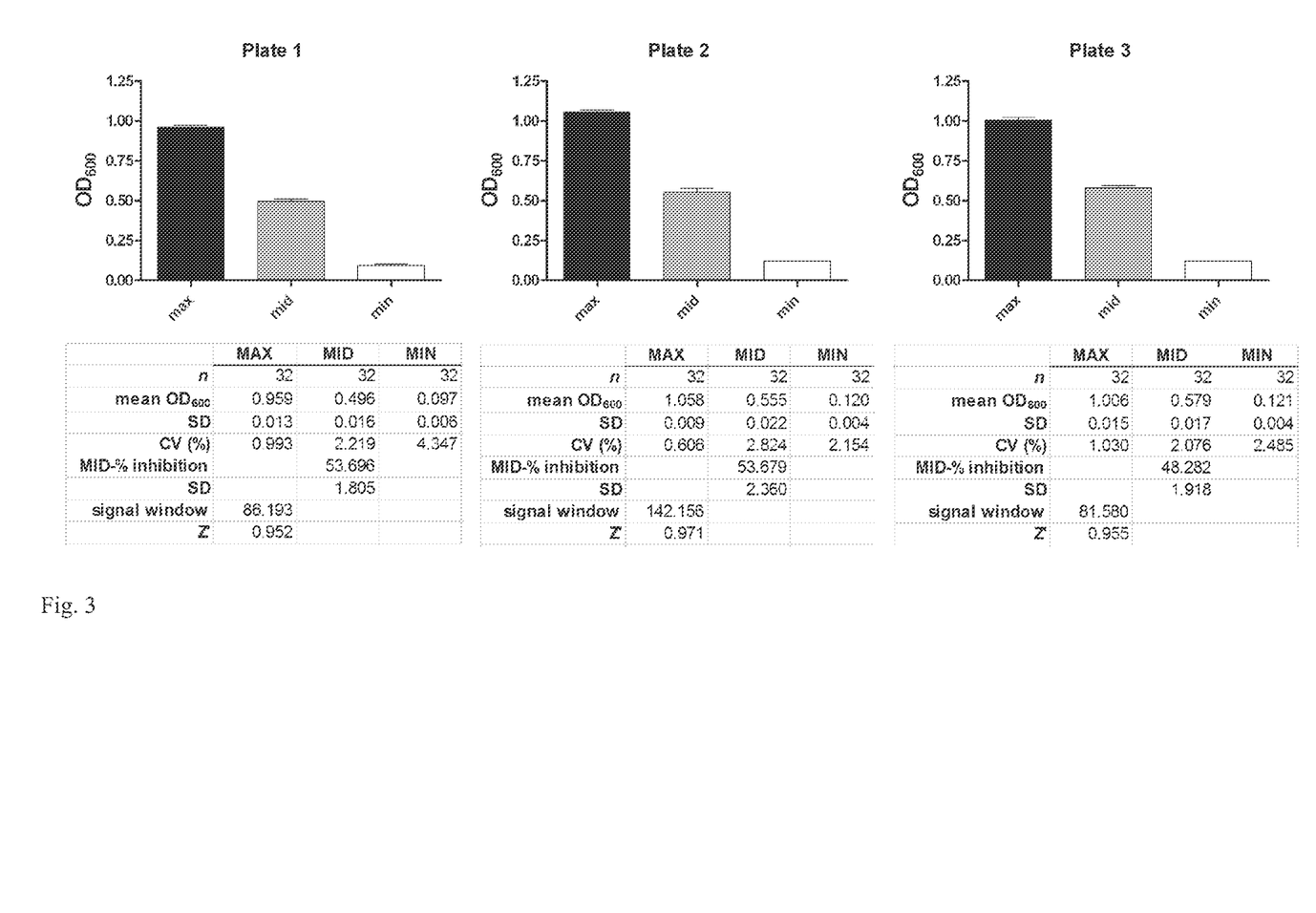

Plate Uniformity and Signal Variability Assessment: To assess the plate uniformity three 96 well plates we prepared using the interleaved signal format described on the NIH National Center for Translational Therapeutics (NCTT) website (assay.nih.gov/assay/index.php/Section2:Plate_Uniformity_and_Signal_Variability_Assessmen t). Initially, each well had 200 μl of WT cells+YPD media+1% DMSO (v/v). The initial cell density was 3×10⁶ cells/ml. Wells were considered "max" growth with no 5-FUrd; "mid" with 50 μM 5-FUrd; "min" with 1 mM 5-FUrd. The plates were allowed to grow for 10 hrs before reading $OD_{600}$ with a BioRad Benchmark Plus microtiter plate reader. The plates have excellent uniformity both within and between plates. The $OD_{600}$ means for the "max" growth wells ranged from 0.96 to 1.06, for "mid" growth wells from 0.50 to 0.58, and for "min" growth wells from 0.10 to 0.12 (FIG. 3). The Coefficient of Variation (CV)=(SD/n½)/mean where SD=standard deviation and n=number of wells. For all conditions the CV was <1%, well below the 20% maximally acceptable CV. There was no evidence of edge effects in the wells containing similar conditions. Similarly the standard parameters for signal variability in a high throughput screen were significantly better than the minimum acceptable levels set by NCTT for a potential HTS. The Signal Window (SW), where SW=[($Avg_{max}$−3*$SD_{max}$/√n)−($Avg_{min}$+3*$SD_{min}$/√n)]/($SD_{max}$/√n) [18] was >81 for all three plates (FIG. 9), well above the SW>2 required by NCTT. The Z' scores, where Z'=[($Avg_{max}$−3*$SD_{max}$/√n)−($Avg_{min}$+3*$SD_{min}$/√n)]/($Avg_{max}$−$Avg_{min}$), were all >0.95 (FIG. 3), well above the minimally acceptable score of 0.4 determined by NCTT for a HTS. Thus, the yeast assay displays the necessary plate uniformity and minimal signal variability for a viable HTS based on the criteria set by NCTT.

5-FUrd Stability. Stability of 5-FUrd under the assay conditions is essential. The assay will involve yeast growth in the presence of 5-FUrd for 10-16 hrs at 30° C. To test 5-FUrd stability a sample of 5-FUrd was split into two aliquots. One was stored at −20° C. and the other at 30° C. for 90 hrs. The 5-FUrd $IC_{50}$ was then determined for WT yeast as described above. The $IC_{50}$s were 46±2 μM (−20° C. sample) and 60±3 μM (n=3) (30° C. sample). Thus, 5-FUrd is stable under the assay growth conditions for at least 90 hrs. The assay should only require 10-16 hrs of growth, so 5-FUrd is stable on the timescale of the assay.

DMSO effects: Compounds in high throughput screening chemical libraries are usually dissolved in DMSO. The final DMSO concentration maybe as high as 1% in a typical high throughput screen. It was verified that 1% DMSO did not significantly affect yeast growth. Experiments in FIG. 3 were performed in the presence of 1% DMSO. Also examined was the effect of 1% DMSO on PfENT1 function in the *Xenopus* oocyte uptake assay. Uptake of [H³]adenine by PfENT1-expressing oocytes was similar in the absence and presence of 1% DMSO (v/v) (two-tailed Student's t-test, p-value=0.08). Thus, the DMSO solvent added in the HTS should not affect PfENT1 function or yeast growth.

Figure 4:
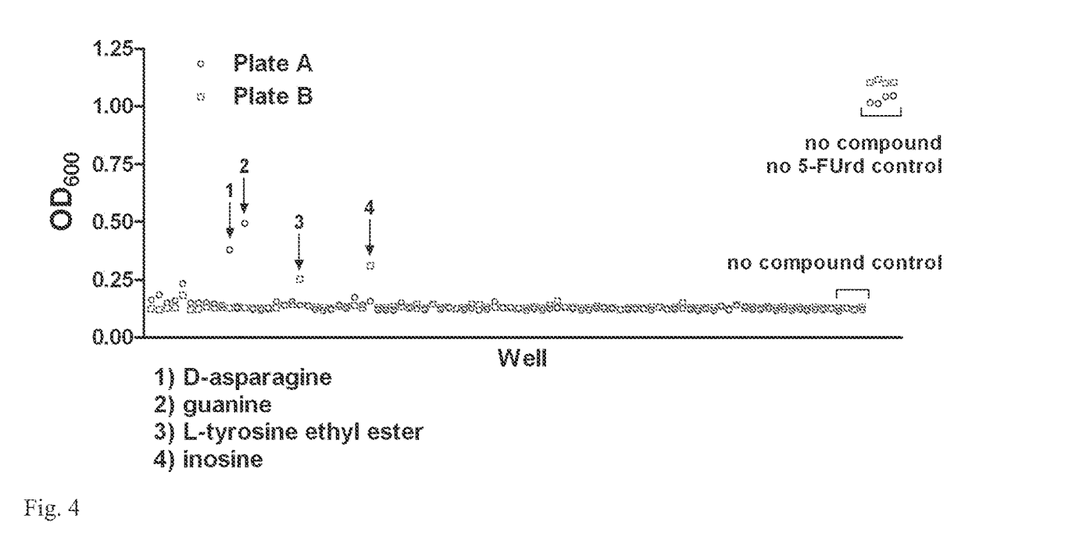
FIG. 4. Results of pilot screen with 176 compound library. Wells 1 to 96 on x-axis. Results from 2 plates with different compounds shown.

176 Compound Library. A study was conducted with a 176 compound library obtained from the Einstein Macromolecular Therapeutics Core facility. The compounds were added at a concentration of 25 μM with 125 μM 5-FUrd/well. FIG. 4 shows the $OD_{600}$ for each well following 16 hrs of growth. Four compounds showed $OD_{600}$>5 SD of the "no compound" control. Two, guanine and inosine, are likely to be competitive inhibitors of PfENT1 transport of 5-FUrd because they are substrates for PfENT1. The molecular basis for inhibition by the other two compounds remains to be determined.

MMV Toolbox Compound Library. Medicines for Malaria Ventures created a 400 compound library that they provide free of charge to investigators (world wide web.mmv.org/malariabox).

Figure 5:
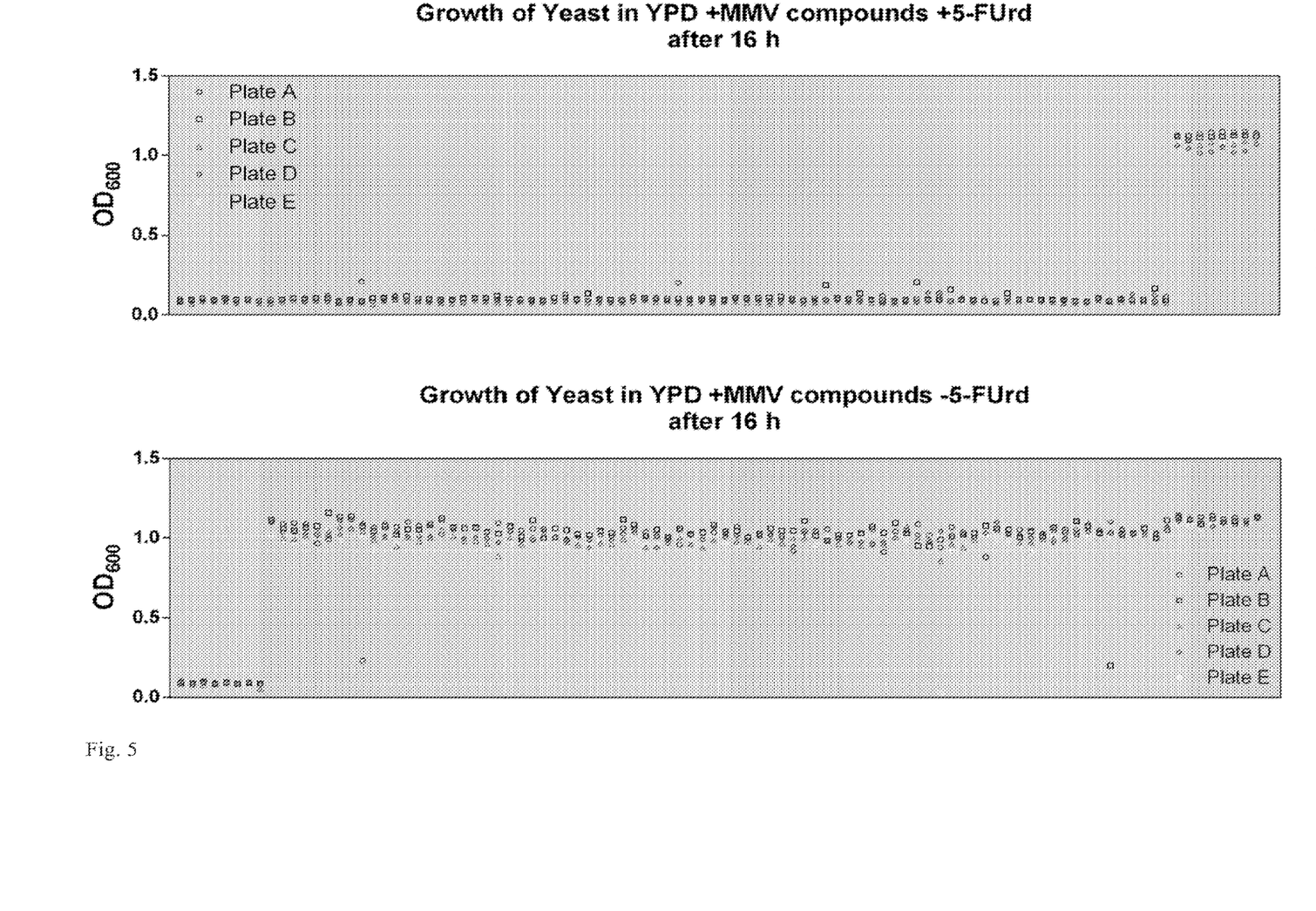
FIG. 5. Scatter plot results of pilot screen with the 400 compound MMV library. Wells 1 to 96 on x-axis. Results from 5 plates with different compounds shown. Top panel, growth in the presence of 125 µM 5-FUrd. Bottom panel, growth in the presence of the 400 compounds but in the absence of 5-FUrd to look for compound toxicity towards the yeast. Two compounds display significant toxicity. The points for the final 8 well in the top panel and the initial 8 wells in the bottom panel are controls, without (top) and with (bottom) 5-FUrd.

The library was used in a screen as described above with the compounds at a concentration of 20 As seen in FIG. 5, none of the wells except the controls lacking 5-FUrd (far right points, top panel) showed significant growth of the PfENT1-expressing fui1Δ yeast. FIG. 5 (bottom panel) demonstrates the toxicity of the compounds for the PfENT1-expressing fui1Δ yeast. The PfENT1-expressing fui1Δ yeast were grown in the presence of 20 μM concentration of the 400 compounds. Growth was significantly inhibited by two compounds.

Accordingly, the system has been demonstrated to successfully identify ENT inhibitors from a library of test agents.

Example 2

Another assay to identify inhibitors of an Equilibrative Nucleoside Transporter (ENT) is further provided. In this assay the ENT is able to transport a purine nucleoside such as adenosine. The rationale for the assay is that yeast lack the ability to transport adenosine into the cell. Mutant purine-auxotrophic yeast, unable to perform de novo purine biosynthesis, will be unable to grow in media where the only purine source is a nucleoside such as adenosine. However, they will be able to grow in media supplemented with a nucleobase such as adenine because yeast have endogenous transporters for nucleobases. For this purpose, a purine-auxotrophic yeast can be generated by knocking out any one of the essential enzymes in the yeast de novo purine biosynthetic pathway. By expressing an ENT capable of transporting adenosine in the purine-auxotrophic yeast, the ENT-expressing purine-auxotrophic yeast can now grow in the presence of adenosine.

The ENT-expressing purine-auxotrophic yeast form the basis for this high throughput screening assay. In the presence of adenosine these yeast will grow, but the presence of an ENT inhibitor will prevent the growth of the ENT-expressing purine auxotrophic yeast. By making these yeast express a marker, such as a Green Fluorescent Protein (GFP) variant, yeast growth can be assessed either 1) by turbidity that can be measured by the optical density at around 600 nm ($OD_{600}$) or 2) by GFP variant fluorescence intensity, or both. The assay can be performed in a variety of high throughput screening plates at various well densities (for example, 96, 384 or 1536).

Purine-auxotrophic yeast have been generated herein by a knockout of the yeast ade2 gene (YOR128C, phosphoribosylaminoimidazole carboxylase) in the yeast de novo purine biosynthetic pathway. The ade2 knockout yeast (ade2Δ) can grow on adenine imported by endogenous yeast nucleobase transporters but cannot grow on the nucleoside adenosine because yeast lack the ability to transport adenosine.

Figure 6:
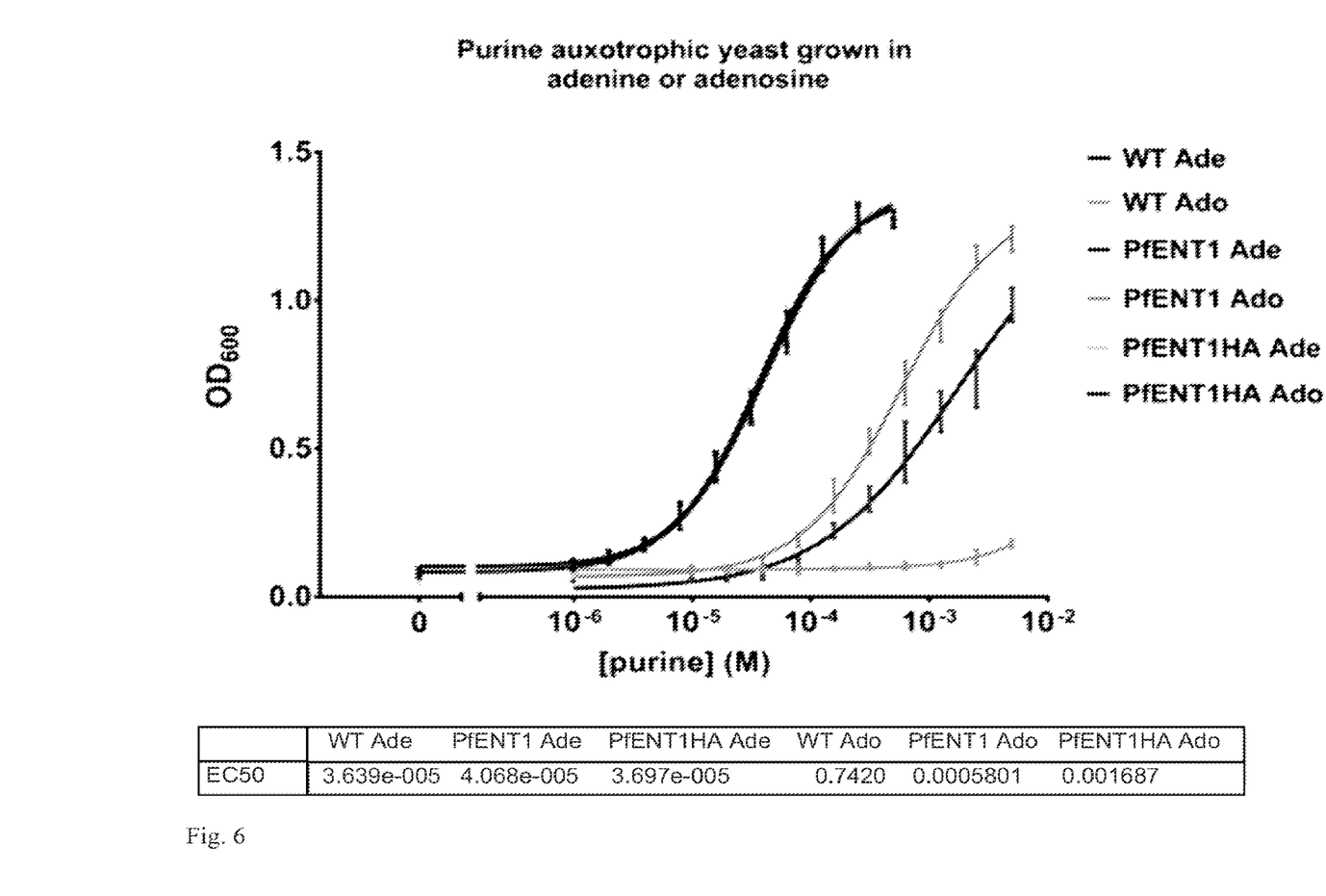
FIG. 6. Illustration of the growth of PfENT1-expressing ade2Δ yeast with increasing concentrations of adenosine in the growth media. The green line shows that ade2Δ yeast do not grow on adenosine (Ado), whereas the yeast expressing either PfENT1 (blue line) or a C-terminal HA epitope tagged PfENT1 (dark green) do grow. All three yeast strains grow on adenine (Ade).

Expression of the malaria Plasmodium falciparum Equilibrative Nucleoside Transporter Type 1 (PfENT1), which can transport adenosine, into ade2Δ yeast allows them to grow in the presence of adenosine. In this assay, inhibitors of PfENT1 prevent yeast growth. Hits are identified by the lack of yeast growth. The adenosine concentration dependence of the growth of these PfENT1-expressing ade2Δ yeast is illustrated in FIG. 6.

Secondary assays can also be employed to reduce false-positives, for example, growth of the purine-auxotrophic yeast in the presence of adenine. Any compound that inhibited growth of these yeast in the presence of adenine, which can be transported outside of the ENT system, would not be an ENT inhibitor.

The assays can be employed to find inhibitors of the parasites described herein. In an example, *Cryptosporidium* is a genus of unicellular, intracellular, protozoan parasites that causes gastrointestinal symptoms and diarrhea in humans and various domesticated animals. *Cryptosporidium* parasites are purine auxotrophs, unable to perform de novo purine biosynthesis. They import purine precursors from the host cell via equilibrative nucleoside transporters (ENTs). A subset of purine salvage pathway enzymes convert the imported purines into those needed for DNA and RNA synthesis and other cellular metabolic processes. Ihibition of purine entry will impair or kill the parasites. The main *Cryptosporidium* species that infect humans are *C. parvum* and *C. hominis*, but other *Cryptosporidium* species can infect humans. There is a single gene encoding an equilibrative nucleoside transporter in *C. parvum* and *C. hominis*. Expression of the *Cryptosporidium* ENT in yeast permits a high throughput screen for inhibitors that may kill *Cryptosporidium* parasites. Such inhibitors are likely useful in treating *Cryptosporidium*-induced diarrhea and gastrointestinal symptoms in humans and domesticated animals.

Example 3

Inhibitors of purine transport proteins for other purine auxotrophic human and animal parasites: Many human and animal eukaryotic parasites are purine auxotrophs. Purine auxotrophic parasites are unable to synthesize the purines needed for DNA and RNA synthesis and other cellular metabolic processes. Purine auxotrophic parasites must import purines from their host cell or organism. They use one or more membrane transport proteins that are able to transport purine nucleobases or nucleosides across the parasite plasma membrane and into the parasite cytoplasm. These transport proteins may either be equilibrative/facilitative transporters or concentrative transporters. Once in the parasite cytoplasm the purines are transformed through branches of the purine salvage pathway into the purines required by the parasite for cellular metabolic processes. Because the parasites require purine import in order to grow, inhibiting the purine transporters may be a useful strategy to develop drugs to treat the illnesses caused by these parasites. The assays disclosed herein can identify inhibitors of purine transporters which can be used as drugs themselves to treat purine auxotrophic parasites that are pathogenic to humans or animals.

Non-limiting examples of purine auxotrophic parasites whose purine transport proteins are useful drug targets include parasites from the following genera: *Cryptosporidium, Entamoeba, Leishmania, Plasmodium, Schistosoma, Trypanasoma*, and *Toxoplasma*.

The assays described herein for *Plasmodium falciparum* can be performed with the purine transporters from the relevant pathogenic purine auxotrophic parasite by replacing the *Plasmodium falciparum* transporter in the two yeast strains, fui1Δ and ade2Δ, or any other critical gene in the yeast de novo purine biosynthetic pathway (e.g. a *Saccharomyces cerevisiae* ADE4; ADE5; ADE7; ADE8; ADE6; ADE1; ADE2; ADE13; ADE16; ADE17; or ADE12; or an equivalent gene of one thereof in another yeast strain).

The basic preferences for the assay are 1) the transporter transports a substance that is cytotoxic to yeast (such as, but not limited, to 5-flurouridine or tubercidin), 2) it must be possible to generate yeast that do not transport the cytotoxic substance, for example by knocking out one or more endogenous yeast transport genes, and 3) one must be able to functionally express the transporter in yeast. When these three conditions are met, then either or both assays can be used to screen chemical libraries to identify purine transporter inhibitors. These inhibitors may serve as antiparasitic drugs.

Example 4

High Throughput Screening Statistics. The primary assay was performed with PfENT1-expressing fui1Δ yeast, using >10 mM inosine as a positive growth control in 384-well plates. Table 1 below contains the information on the robustness of the assay based on high throughput screening criteria in the NIH National Center for Translational Therapeutics (NCTT) website: (assay.nih.gov/assay/index.php/Section2:Plate_Uniformity_and_Signal_Variability_Assessmen t). Each row in the Table below represents the data from a separate 384-well plate with wells containing minimal, maximal and approximately 50% of maximal growth by adding inosine to the mid (~4 mM) and maximal wells (>10 mM). The data in the left hand half were obtained using GFP fluorescence to detect the growth of the yeast, which express GFP. The data in the right hand half were obtained using the $OD_{620}$ to detect yeast growth. SD=standard deviation; CV %=Coefficient of Variation; SW=signal window; and Z' is a measure of robustness (Achyuthan K E, Whitten D G (2007) Design considerations for high-throughput screening and in vitro diagnostic assays. Comb Chem High Throughput Screen 10: 399-412.)

TABLE 1

Robustness of the assay based on high throughput screening criteria

|  |  | RFU | Min | Mid | Max | $OD_{620}$ | Min | Mid | Max |
|---|---|---|---|---|---|---|---|---|---|
| Plate 1 | mean | 44915.10 | 208450.18 | 513629.04 | mean | 0.08 | 0.67 | 1.37 |
|  | SD | 2496.51 | 32086.37 | 4313.02 | SD | 0.01 | 0.06 | 0.03 |
|  | CV % | 0.49 | 1.36 | 0.07 | CV % | 1.52 | 0.85 | 0.17 |
|  | SW |  | 103.94 |  | SW |  | 43.07 |  |
|  | Z' |  | 0.96 |  | Z' |  | 0.90 |  |
| Plate 2 | mean | 44664.86 | 207679.97 | 513148.08 | mean | 0.09 | 0.64 | 1.36 |
|  | SD | 2678.57 | 38246.07 | 5293.06 | SD | 0.02 | 0.09 | 0.04 |
|  | CV % | 0.53 | 1.63 | 0.09 | CV % | 1.61 | 1.24 | 0.29 |
|  | SW |  | 83.99 |  | SW |  | 23.98 |  |
|  | Z' |  | 0.95 |  | Z' |  | 0.85 |  |
| Plate 3 | mean | 46031.32 | 228980.53 | 511128.84 | mean | 0.09 | 0.72 | 1.38 |
|  | SD | 2516.08 | 41442.64 | 6961.22 | SD | 0.01 | 0.08 | 0.04 |
|  | CV % | 0.48 | 1.60 | 0.12 | CV % | 1.42 | 1.03 | 0.23 |
|  | SW |  | 62.73 |  | SW |  | 31.88 |  |
|  | Z' |  | 0.94 |  | Z' |  | 0.88 |  |

The recombinant yeasts and methods in the Examples herein can be made and performed with a concentrative nucleoside transporter (CNT) in place of the ENT, mutatis mutandis.

REFERENCES

1. Baldwin S A, Beal P R, Yao S Y, King A E, Cass C E, et al. (2004) The equilibrative nucleoside transporter family, SLC29. Pflugers Arch 447: 735-743.
2. Pastor-Anglada M, Cano-Soldado P, Errasti-Murugarren E, Casado F J (2008) SLC28 genes and concentrative nucleoside transporter (CNT) proteins. Xenobiotica 38: 972-994.
3. Carter N S, Yates P, Arendt C S, Boitz J M, Ullman B (2008) Purine and pyrimidine metabolism in *Leishmania*. Adv Exp Med Biol 625: 141-154.
4. Landfear S M, Ullman B, Carter N S, Sanchez M A (2004) Nucleoside and nucleobase transporters in parasitic protozoa. Eukaryot Cell 3: 245-254.
5. Cass C E, Young J D, Baldwin S A (1998) Recent advances in the molecular biology of nucleoside transporters of mammalian cells. Biochem Cell Biol 76: 761-770.
6. Cass C E, Young J D, Baldwin S A, Cabrita M A, Graham K A, et al. (1999) Nucleoside transporters of mammalian cells. Pharm Biotechnol 12: 313-352.
7. Cassera M B, Zhang Y, Hazleton K Z, Schramm V L (2011) Purine and pyrimidine pathways as targets in *Plasmodium falciparum*. Current topics in medicinal chemistry 11: 2103-2115.
8. El Bissati K, Zufferey R, Witola W H, Carter N S, Ullman B, et al. (2006) The plasma membrane permease PfNT1 is essential for purine salvage in the human malaria parasite *Plasmodium falciparum*. Proc Natl Acad Sci USA 103: 9286-9291.
9. El Bissati K, Downie M J, Kim S K, Horowitz M, Carter N, et al. (2008) Genetic evidence for the essential role of PfNT1 in the transport and utilization of xanthine, guanine, guanosine and adenine by *Plasmodium falciparum*. Mol Biochem Parasitol 161: 130-139.
10. Hyde R J, Cass C E, Young J D, Baldwin S A (2001) The ENT family of eukaryote nucleoside and nucleobase transporters: recent advances in the investigation of structure/function relationships and the identification of novel isoforms. Mol Membr Biol 18: 53-63.
11. Casado F J, Lostao M P, Aymerich I, Larrayoz I M, Duflot S, et al. (2002) Nucleoside transporters in absorptive epithelia. J Physiol Biochem 58: 207-216.
12. Kong W, Engel K, Wang J (2004) Mammalian nucleoside transporters. Curr Drug Metab 5: 63-84.
13. Molina-Arcas M, Casado F J, Pastor-Anglada M (2009) Nucleoside transporter proteins. Curr Vasc Pharmacol 7: 426-434.
14. Vickers M F, Yao S Y, Baldwin S A, Young J D, Cass C E (2000) Nucleoside transporter proteins of *Saccharomyces cerevisiae*. Demonstration of a transporter (FUI1) with high uridine selectivity in plasma membranes and a transporter (FUN26) with broad nucleoside selectivity in intracellular membranes. J Biol Chem 275: 25931-25938.
15. Zhang J, Smith K M, Tackaberry T, Sun X, Carpenter P, et al. (2006) Characterization of the transport mechanism and permeant binding profile of the uridine permease Fuilp of *Saccharomyces cerevisiae*. J Biol Chem 281: 28210-28221.
16. Riegelhaupt P M, Cassera M B, Frohlich R F, Hazleton K Z, Hefter J J, et al. (2010) Transport of purines and purine salvage pathway inhibitors by the *Plasmodium*

*falciparum* equilibrative nucleoside transporter PfENT1. Mol Biochem Parasitol 169: 40-49.
17. Janke C, Magiera M M, Rathfelder N, Taxis C, Reber S, et al. (2004) A versatile toolbox for PCR-based tagging of yeast genes: new fluorescent proteins, more markers and promoter substitution cassettes. Yeast 21: 947-962.
18. Achyuthan K E, Whitten D G (2007) Design considerations for high-throughput screening and in vitro diagnostic assays. Comb Chem High Throughput Screen 10: 399-412.
19. Frame I J, Merino E F, Schramm V L, Cassera M B, Akabas M H (2012) Malaria parasite type 4 equilibrative nucleoside transporters (ENT4) are purine transporters with distinct substrate specificity. Biochem J. 446(2):179-90.

What is claimed is:

1. A method for identifying an agent as an inhibitor of an equilibrative nucleoside transporter (ENT) comprising
    contacting a recombinant yeast, in the presence of a cytotoxic nucleoside and in a yeast culture medium with the agent for a first time period under conditions permitting yeast growth,
    wherein the cytotoxic nucleoside is present in the yeast growth medium at a level which has been predetermined to be a minimum concentration of cytotoxic nucleoside that causes complete killing of the recombinant yeast,
    and wherein the recombinant yeast comprises a deletion of a yeast de novo purine biosynthetic pathway gene in a genome thereof and expresses a heterologous equilibrative nucleoside transporter (ENT), wherein the gene is a fui1 gene or *Saccharomyces cerevisiae ADE*4; ADE5; ADE7; ADE8; ADE6; ADE1; ADE2; ADE13; ADE16; ADE17; or ADE12 gene:
    quantifying the growth of the recombinant yeast in the presence of the agent;
    comparing the growth of the recombinant yeast in the presence of the agent to the growth of the recombinant yeast for a second predetermined time period in the absence of the agent; and
    identifying the agent as an inhibitor or not of the ENT, wherein an increased growth in the presence of the agent as compared to in the absence of the agent indicates that the agent is an inhibitor of the ENT, and wherein no growth in the presence of the agent as compared to in the absence of the agent indicates that the agent is not an inhibitor of the ENT.

2. The method of claim 1, wherein the growth of the recombinant yeast is measured indirectly by quantifying optical density (OD) of the medium containing the recombinant yeast.

3. The method of claim 1, wherein the agent is a small organic molecule of 2000 daltons or less.

4. The method of claim 1, further comprising determining if an agent identified by the method as an inhibitor of the ENT inhibits growth of, or kills, a parasite in which the ENT is found in the wild type thereof, comprising contacting the parasite with the agent identified by the method as an inhibitor and determining the growth or viability of the parasite in the presence of the agent, wherein an agent identified by the method as an inhibitor and which inhibits growth of, or kills, the parasite, is identified as an inhibitor of the growth of, or killer of, the parasite.

5. The method of claim 1, wherein the cytotoxic nucleoside is 5-fluorouridine, 7-deazaadenosine or tubercidin.

6. The method of claim 1, wherein the yeast is *Saccharomyces cervisiae*.

7. The method of claim 1, wherein the heterologous ENT is a parasite ENT, or wherein the heterologous CNT is a parasite CNT.

8. The method of claim 1, wherein the parasite is a purine auxotroph.

9. The method of claim 1, wherein the parasite is a *Plasmodium* sp., *Leishmania* sp., *Trypanasoma* sp., *Toxoplasma* sp., *Entamoeba* sp., *Schistosoma* sp., or *Cryptosporidium* sp.

10. The method of claim 1, wherein the ENT is *Plasmodium falciparum* ENT type 1.

* * * * *